United States Patent
Vinayak et al.

(10) Patent No.: US 9,249,439 B2
(45) Date of Patent: Feb. 2, 2016

(54) PROCESS OF CULTIVATING BACTERIA FOR YIELD IMPROVEMENT OF CAPSULAR POLYOSES

(75) Inventors: Kapre Subhash Vinayak, Pune (IN); Swapan Kumar Jana, Pune (IN); Amar Kumar Srivastava, Pune (IN)

(73) Assignee: Serum Institute of India Ltd., Pune (IN)

( * ) Notice: Subject to any disclaimer, the term of this patent is extended or adjusted under 35 U.S.C. 154(b) by 0 days.

(21) Appl. No.: 14/365,959

(22) PCT Filed: Dec. 15, 2011

(86) PCT No.: PCT/IN2011/000861
§ 371 (c)(1),
(2), (4) Date: Jun. 16, 2014

(87) PCT Pub. No.: WO2013/088448
PCT Pub. Date: Jun. 20, 2013

(65) Prior Publication Data
US 2014/0342411 A1  Nov. 20, 2014

(51) Int. Cl.
C12N 1/00 (2006.01)
C12P 19/04 (2006.01)
C12P 19/00 (2006.01)
C12N 1/20 (2006.01)

(52) U.S. Cl.
CPC . *C12P 19/04* (2013.01); *C12N 1/20* (2013.01); *C12P 19/00* (2013.01)

(58) Field of Classification Search
None
See application file for complete search history.

(56) References Cited

U.S. PATENT DOCUMENTS

2007/0065460 A1* 3/2007 Hamidi et al. ............. 424/234.1
2008/0312137 A1* 12/2008 Swennen ........................ 514/8
2010/0063270 A1* 3/2010 Costantino ................. 536/123.1
2010/0158953 A1 6/2010 Crinean
2010/0272755 A1 10/2010 Costantino et al.

OTHER PUBLICATIONS

International Search Report dated May 21, 2012 for PCT/IN11/00861.
International Preliminary Report on Patentability dated Jun. 17, 2014 for PCT/IN11/00861.
Sigma-Aldrich "Dulbecco's Modified Eagle's Medium (DME)" Product No. D7777, Apr. 2007.

* cited by examiner

*Primary Examiner* — Chris R Tate
*Assistant Examiner* — Douglas F White
(74) *Attorney, Agent, or Firm* — Kinney & Lange, P.A.

(57) ABSTRACT

The invention relates to optimization of culture conditions that utilizes different feed solutions and feeding strategies for improving capsular polyoses (CP) production.

14 Claims, 3 Drawing Sheets

PROCESS OF CULTIVATING BACTERIA FOR YIELD IMPROVEMENT OF CAPSULAR POLYOSES

BRIEF DESCRIPTION

Capsular polyoses are important immunogens found on the surface of bacteria involved in various bacterial diseases. This feature has led to them being an important component in the design of vaccines. They have proved useful in eliciting immune responses especially when linked to carrier proteins.

Typically, capsular polyoses are produced using batch culture in complex medium [Refer Shen et al. 2001 *Vaccine* 19:850-61; Palazzi et al. 2004 *J. Infect. Dis.* 190:558-64; Merritt et al. 2000 *J. Biotech.* 81:189-97; Dassy & Fournier 1996 *Infect. Immunol.* 64:2408-14; Suarez et al. (2001) Appl. Env. Microbiol. 67:969-71; Wicken et al. (1983) *J. Bact.* 153:84-92] The traditional DO-stat control of nutrient feeding is simply based on the concept of DO rises/spikes (due to a reduction of carbon substrate or cessation of oxygen consumption or respiration) upon nutrient limitation or depletion. The DO-stat control tries to maintain the culture at a constant DO level within a limit (the DO setpoint) by increasing the nutrient feed rate when DO rises above the setpoint and reducing the nutrient feed rate when DO drops below the setpoint. The DO-stat strategy typically works well in defined media where nutrient depletion results in rapid DO rise. However, the DO-stat method often fails in media supplemented with rich complex nutrients such as yeast extract, tryptone, peptone, casamino acid, or Hy-Soy. Rich complex nutrients are capable of supporting cellular maintenance and respiration through amino acid catabolism such that the DO level remains low (i.e. no apparent DO spikes) even under carbon source limitation or depletion.

When a complex medium is used for culture growth, a pH-stat strategy may be more suitable than DO-stat since the culture pH tends to increase once the carbon source is depleted. In a manner similar to DO-stat control, the pH-stat method maintains a constant culture pH at about the setpoint by increasing the nutrient feed rate as pH rises above the setpoint and reducing the nutrient feed rate when pH drops below the setpoint. However, since the change in culture pH upon nutrient depletion is less responsive than that of DO, feeding control by pH-stat can be relatively sluggish when compared to DO-stat.

Most studies used batch culture systems in which the growth rate, nutrient levels and metabolic concentrations change during cultivation. In such systems, alteration of one factor results in changes in other factors associated with growth that can affect yields unpredictably. Continuous cultures allow the researcher to separate and define parameters that are interdependent during batch culture growth, such as growth rate, nutrient and product concentrations and cell density. During continuous culture, fresh medium is added to a culture at a fixed rate and cells and medium are removed at a rate that maintains a constant culture volume.

In perfusion culture, fresh medium is added to a culture at a fixed rate and cell-free spent medium are removed at a rate that maintains a constant culture volume. However, continuous and perfusion culture is prone to strain stability problems and contamination, and is somewhat expensive due to the continuous feed of medium and nutrients. Therefore, there is a need to find alternatives to continuous culture for the high yield production of capsular polysaccharides in order to overcome the problems with continuous culture that are cited above.

One approach to overcome the drawbacks of continuous culture is exemplified in WO 2007/052168. A complex fed batch fermentation process has been developed to maintain a nutritional environment and a growth rate favorable to cps production. This process combines the advantages of batch and continuous techniques, producing high cell densities due to extension of the exponential growth phase and to conditions that control substrate addition during fermentation. However, the complex fed batch technique uses software with a complex algorithm to manage the fermentation.

Another approach is disclosed in WO 20100272755. A method for cultivating the bacteria has been developed, wherein the cultivation comprises two instantaneous additions of yeast extract, followed by a linear addition of a glucose. Each addition is initiated at a designated OD level. Thus here, the linear addition of a carbon source without an algorithm is an improvement over the previous complex fed batch fermentation. However, this is a very tedious method requiring continuous measurement of O.D. Further it fails to consider the constant changing requirements (microenvironment) of organism.

The instant invention is based on a surprising finding and relates to a novel feeding method, wherein the rate of feed medium addition during fed-batch fermentation is equivalent to the rate of alkali mixture addition for maintaining a preset pH resulting in a volumetric increase in CP yield as compared to previously existing batch fermentation methods.

SUMMARY OF THE INVENTION

The instant invention provides a novel fed batch fermentation strategy resulting in 3 to 5 times increase in productivity of capsular polyoses as compared to batch mode fermentation.

Particularly, the instant method relates to a method of cultivating capsulated bacteria for higher volumetric production of capsular polyoses (CP), wherein said method comprises (a) providing an inoculum of a strain of bacteria expressing the CP; (b) cultivating the strain by fermentation at pH 7.2, wherein the rate of feed medium addition is equivalent to the rate of alkali mixture addition for maintaining a preset pH; c) fermenting the culture medium at 35-38° C. under stirring at 50-150 RPM with an air flow rate of 0.1-0.5 vvm.

DETAILED DESCRIPTION OF INVENTION

Figure 1:
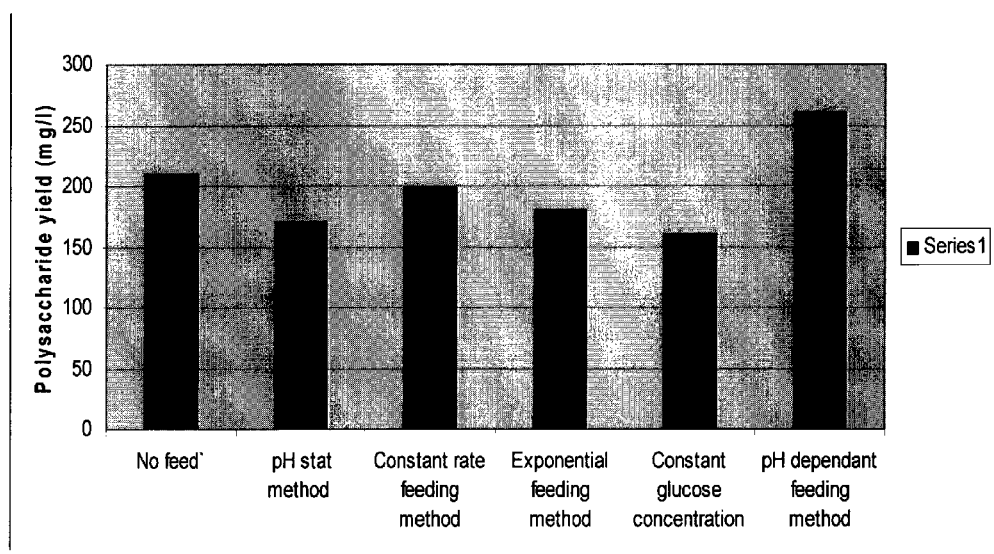
FIG. 1: Pneumococcal serotype 1 polysaccharide (fed-batch fermentation) for different feeding methods
Figure 2:
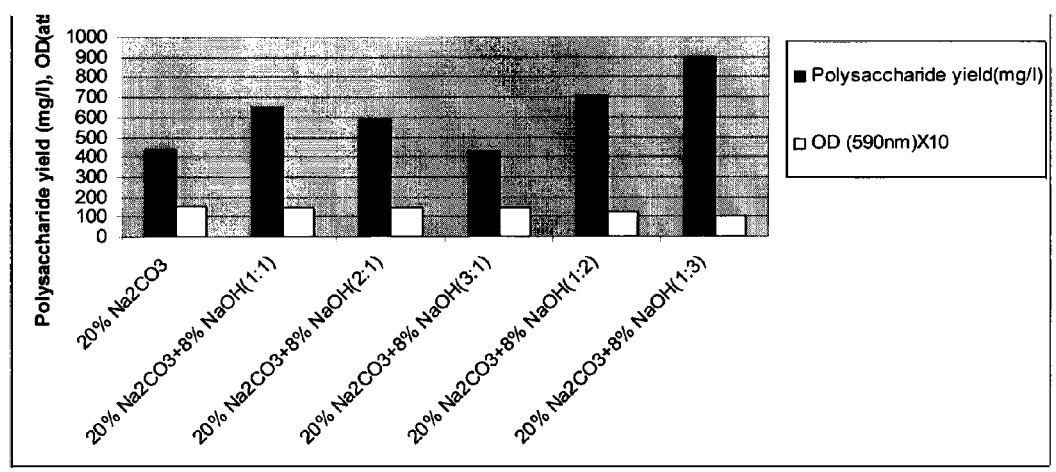
FIG. 2: Pneumococcal serotype 1 polysaccharide yield (fed-batch) for different ratios of bases in alkali mixture for maintaining pH.
Figure 3:
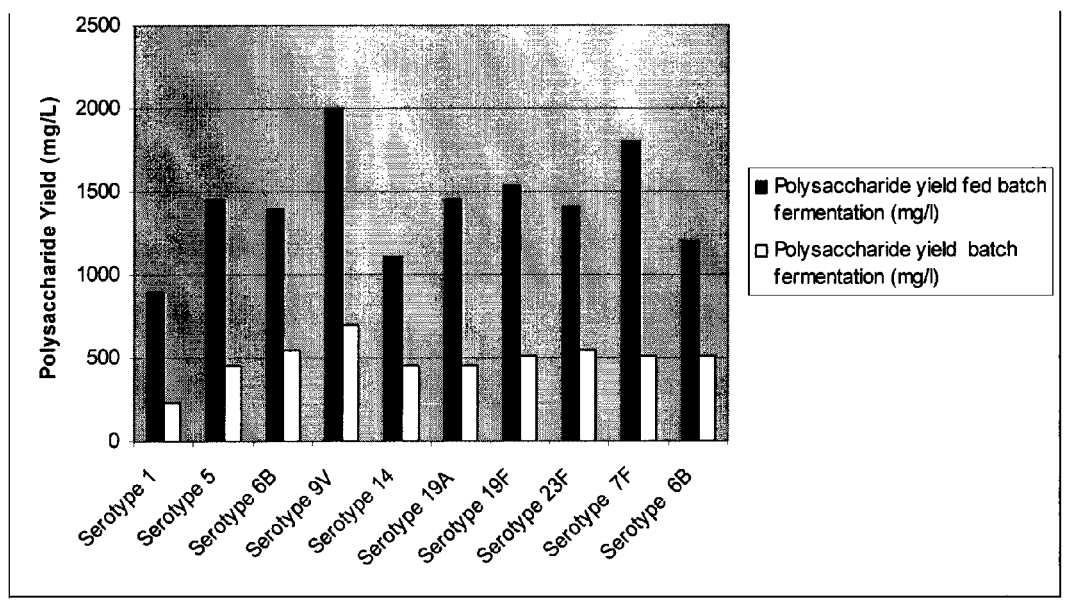
FIG. 3: Pneumococcal serotype 1, 5, 6A, 6B, 7F, 9V, 14, 19A, 19F and 23F polysaccharide yield by fed-batch as compared to batch fermentation.

The disclosure provides a process of cultivating bacteria, wherein the rate of feed addition during fed-batch fermentation is equivalent to the rate of alkali mixture addition for maintaining a preset pH.

Another aspect of the instant invention is that alkali mixture consisting of NaOH and Na2CO3 in a specific ratio can be used for a) maintaining preset pH & b) obtaining higher capsular polyose yield. Use of only Na2CO3 can provide suitable medium for growth as well as pH control, however the limiting condition of Na2CO3 can provide a stress condition to make capsular polyoses and higher requirement of Na2CO3 quantity. Hence when the mixture of NaOH and Na2CO3 is used for maintaining pH, the growth can be less with higher specific polyose productivity as well as with higher volumetric productivity due to less quantity of alkali consumption.

As per the instant process, when glucose gets converted to lactic acid and pH begins to decrease, it can be maintained by alkali mixture addition with simultaneous glucose addition to supplement the depleted glucose in media.

In a preferred embodiment of the instant invention, the fermentation feed components can comprise of at least one carbon source, at least one nitrogen source, at least one magnesium source that can be fed to the batch fermentation at a particular cell density at a feed rate equivalent to the rate of alkali mixture addition.

One embodiment of the current invention is that, said alkali mixture contains at least two bases selected from the group consisting of sodium hydroxide, sodium carbonate, sodium bicarbonate, potassium hydroxide, potassium carbonate and calcium hydroxide. Also a designated ratio of sodium hydroxide and sodium carbonate is selected to achieve a higher volumetric production of CP.

The designated ratio of sodium hydroxide to sodium carbonate can be between 1:1 and 4:1.

According to the instant invention, NaOH was further enhancing the productivity of CP when it was used with Na2CO3 as mixture for maintaining the pH. Only Na2CO3 was providing suitable medium for growth when it was used for maintaining the pH. However the limiting condition of Na2CO3 was providing a stress condition to make capsular polyoses. When the mixture of NaOH and Na2CO3 was used for maintaining pH, the growth was less but CP productivity was increased.

Preferably the invention provides a method of culturing *Streptococcus* in fed batch culture, wherein a high yield of CP is produced. Preferably, the yield of cps from the culture medium is between 900 and 2000 mg/L or more. Thus, this fed-batch method allows the production of CP at a volumetric yield increase between 150 and 350% compared with batch culture. In some cases, the yield may be at least twice the quantity produced using batch culture, more preferably 4 times the quantity produced using batch culture.

Another embodiment of the current invention is that the said feed medium can comprise of at least one carbon source, at least one nitrogen source, at least one salt and at least one amino acid.

Preferably the said carbon source is glucose. The nitrogen source can be selected from yeast autolysates, yeast nitrogen base, peptones, tryptone, casamino acids, soybean meal, Hy-Soy, yeast extract and tryptic soy broth. The salt can be selected from potassium sulphate, calcium chloride, magnesium chloride, magnesium sulphate and mixtures thereof.

As per the instant invention the feed medium can comprise of ingredients (gm/l), glucose within a range of 100-500, magnesium sulphate within a range of 1-7.5, Hy-soya within a range of 40-150, yeast extract within a range of 5-50, Thiamine hydrochloride within a range of 0.002-0.005, cysteine within a range of 0.2-0.5, calcium chloride within a range of 0.2-0.5.

Also the feed medium can comprise of ingredients (gm/l), glucose within a range of 100-500, yeast extract within a range of 5-50, Thiamine hydrochloride within a range of 0.002-0.005, cysteine within a range of 0.2-0.5, calcium chloride within a range of 0.2-0.5.

Alternatively said feed medium can comprise of ingredients (gm/l), glucose within a range of 100-500, magnesium sulphate within a range of 0.5-7.5, Hy-soya within a range of 40-150 and yeast extract within a range of 5-50.

A preferred embodiment of the instant invention is that the feed medium can comprise of ingredients (gm/l), glucose within a range of 100-200, magnesium sulphate within a range of 1-3, Hy-soya within a range of 50-150 and yeast extract within a range of 15-25

According to the instant invention the said novel fed batch process can be utilized for preparing capsular polyoses selected from the group consisting of *Escherichia coli, Francisella tularensis, Haemophilus influenzae, Klebsiella, Moraxella catarrhalis, Neisseria meningitidis* groups A, C, $W_{135}$ Y and X, *Porphyromonas gingivalis, Pseudomonas aeruginosa, Burkholderia cepacia, Salmonella typhi, Salmonella typhimurium, Salmonella paratyphi, Shigella dysenteriae, Shigella flexneri, Shigella sonnei, Vibrio cholera, Enterococcus faecalis, Enterococcus faecium,* Group A *Streptococcus,* Group B *Streptococcus, Mycobacterium tuberculosis, Staphylococcus aureus, Staphylococcus epidermidis* and *Streptococcus pneumoniae.*

EXAMPLES

Example 1

Evaluation of Feeding Method for Optimization of Fed Batch Development for *S. Pneumoniae* Serotype 1

Different feeding methods were evaluated for feeding. DO-stat method was not applicable for *S. Pneumoniae* fermentation. As *S. Pneumoniae* is micro-aerofilic bacteria only surface aeration was required during fermentation process. After partial growth of *S. Pneumoniae* in fermenter during batch mode fermentation, dissolved oxygen was around zero.

Five different feeding methods were tried for fed batch fermentation.

1. pH stat method: The pH stat feed was controlled by a set-pH point wherein when the pH of the culture rises above the set-pH, the carbon source was added to the medium and when the pH of the culture falls below the set-pH, the carbon feed was stopped.
2. Constant rate feeding method: In this method 1l concentrated feed was given at 4.2 ml/m for 4 hrs in 1.6 l of broth culture.
3. Exponential feeding method: The feed rate was started with 1 ml/m and increased with OD. The feed rate was increased by 0.5 ml/m for 1 unit increment in OD.
4. Constant glucose concentration: Residual glucose concentration was tried to maintain around 0.5 g/l during fed batch fermentation.
5. pH dependant feeding method: In this method pH was maintained with Na2CO3. The glucose was added for depleted glucose in media at rate which Na2CO3 was fed in media for maintaining the pH.

The NBS Bioflo 115 and Bioengineering AG fermenter was used for all these experiments. The present study was carried out at 3 L NBS Bioflo 115 fermenter model and it was scaled-up to 30 L Bioengineering AG Fermenter. The further scale up could be carried out at 450 L Bioengineering fermenter. The 200 g/l glucose and 5 g/l MgSO4 were used as feeding media for all fed batch fermentation. The fermentation condition were same for all fed batch experiments. The pH was maintained with 20% Na2CO3 solution during fermentation process.

The following parameters were maintained during the fed batch fermentation. Temperature (36.5+0.5), pH (7.1+0.2), RPM-100, Airflow (surface aeration)—0.5 vvm.

TABLE 1

CP yield of serotype 1 for different feeding methods

| Feeding method | CP yield (mg/l) |
|---|---|
| No feed | 210 |
| pH stat method | 170 |
| Constant rate feeding method | 198 |
| Exponential feeding method | 180 |
| Constant glucose concentration | 160 |
| pH dependant feeding method | 260 |

Example 2

Feed Media Optimization for Fed Batch Fermentation of S. Pneumoniae Serotype 1 CP The following different media were used for feeding during fermentation:
1. Glucose—200 g/l
2. Glucose (200 g/l), MgSO4 (2.5 g/l)
3. Glucose—200 g/l, MgSO4—2.5 g/l, Yeast extract—25 g/l.
4. Glucose—100 g/l, MgSO4—5 g/l, Yeast extract—15 g/l, Hy-soya—50 g/l
5. Glucose—200 g/l, MgSO4—2.5 g/l, Yeast extract—25 g/l, Hy-soya—100 g/l
6. Glucose—200 g/l, MgSO4—2.5 g/l, Yeast extract—25 g/l, Hy-soy—100 g/l, Thiamine Hydrochloride—0.02 g/l, Cacl2.2H2O—0.0.02 g/l, Cysteine—0.2 g/l.
7. Glucose—100 g/l, MgSO4—1 g/l, Yeast extract—10 g/l, Hy-soya—40 g/l, Thiamine Hydrochloride—0.04 g/l, Cacl2.2H2O—0.04 g/l, Cysteine—0.4 g/l All the fermentation conditions were maintained as mentioned above. The pH dependent feeding method was used for fed batch fermentation feeding for all batches. The $4^{th}$ Feed medium was utilized for further fed batch experiments.

TABLE 2

CP yield of serotype 1 for different feeding media composition

| Different Feeding Media composition | Capsular Polyose yield (mg/l) |
|---|---|
| 1 | 265 |
| 2 | 385 |
| 3 | 460 |
| 4 | 420 |
| 5 | 400 |
| 6 | 375 |
| 7 | 352 |

Example 3

The Mixture of Alkali Used for Maintaining the pH

The NaOH was further enhancing the productivity of CP when it was used with Na2CO3 as mixture for maintaining the pH. Only Na2CO3 was providing suitable medium for growth when it was used for maintaining the pH. The limiting condition of Na2CO3 was providing a stress condition to make CP. When the mixture of NaOH and Na2CO3 was used for maintaining pH, the growth was less but CP productivity was increased. The 8% NaOH and 20% Na2CO3 was used in ratio of 1:1, 2:1, 3:1 and 4:1. Feed media composition 3 in example 2 was used as feed for the following fed-batches.

TABLE 3

The mixture of alkali used for maintaining the pH for fed batch fermentation of S. Pneumoniae Serotype 1

| | CP yield (mg/l) | OD (590 nm) × 10 |
|---|---|---|
| 20% Na2CO3 | 440 | 154 |
| 20% Na2CO3 + 8% NaOH(1:1) | 650 | 145 |
| 20% Na2CO3 + 8% NaOH(2:1) | 590 | 148 |
| 20% Na2CO3 + 8% NaOH(3:1) | 430 | 145 |
| 20% Na2CO3 + 8% NaOH(1:2) | 705 | 125 |
| 20% Na2CO3 + 8% NaOH(1:3) | 900 | 105 |

Example 4

Different Serotype of S. Pneumoniae were Tried with Optimized Fed Batch Condition For the serotype 1 fed batch conditions were used for other serotype also. The following condition were taken into consideration running the fed batch fermentation.
1. The pH dependant feeding method
2. Mixture of alkali used
3. Optimized feeding media
4. Other fermentation were similar as mentioned above The serotypes 1, 5, 6A, 6B, 7F, 9V, 14, 19A, 19F and 23F were used using new optimized conditions of fed-batch process.

TABLE 4

CP yield in fed batch fermentation for different serotypes

| Serotypes | CP yield batch fermentation (mg/l) | CP fed batch fermentation (mg/l) | Fold increase in CP yield of fed-batch over batch fermentation (mg/l) |
|---|---|---|---|
| Serotype 1 | 228 | 900 | 3.95 |
| Serotype 5 | 450 | 1450 | 3.2 |
| Serotype 6B | 550 | 1400 | 2.54 |
| Serotype 9V | 700 | 2000 | 2.86 |
| Serotype 14 | 450 | 1100 | 2.44 |
| Serotype 19A | 450 | 1450 | 3.2 |
| Serotype 19F | 510 | 1530 | 3 |
| Serotype 23F | 550 | 1410 | 2.56 |
| Serotype 7F | 517 | 1800 | 3.48 |
| Serotype 6A | 508 | 1200 | 2.36 |

Thus fed batch method of the current invention results in volumetric increase in CP yield ranging from 150 to 350%, wherein final CP yield ranges between 900 and 2000 mg/l.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are/therefore intended to be embraced therein.

We claim:

1. A method of cultivating capsulated bacteria for production of capsular polyoses (CP), wherein said method comprises:
   (a) providing an inoculum of a strain of bacteria expressing the CP;
   (b) cultivating the strain in a culture medium to which a feed medium is added by fed-batch fermentation at a preset pH range of 6.9-7.3, whereby an alkali mixture is added to the culture medium at a rate equivalent to that of the feed medium for maintaining the pH range, and wherein the alkali mixture comprises sodium hydroxide and sodium carbonate at a ratio of 3:1; and
   c) fermenting the culture medium at 35-38° C. under stirring at 50-150 RPM with an air flow rate of 0.1-0.5 vvm.

2. The method according to claim 1, wherein a volumetric increase in CP yield is between 150 to 400% as compared to batch or continuous culture conditions.

3. The method according to claim 2, wherein the yield of CP is between 900 mg/l and 2000 mg/l.

4. The method according to claim 1, wherein the feed medium comprises at least one carbon source, at least one nitrogen source, at least one salt and at least one amino acid.

5. The method according to claim 4, wherein the carbon source is glucose.

6. The method according to claim 4, wherein the nitrogen source consists of three or fewer components selected from: yeast autolysates, yeast nitrogen base, peptones, tryptone, casamino acids, soybean meal, Hy-Soy, yeast extract, and tryptic soy broth.

7. The method according to claim 4, wherein the salt is selected from potassium sulphate, calcium chloride, magnesium chloride, magnesium sulphate and mixtures thereof.

8. The method according to claim 4, wherein the feed medium comprises glucose within a range of 100-500 gm/l, magnesium sulphate within a range of 1-7.5 gm/l, Hy-soya within a range of 40-150 gm/l, yeast extract within a range of 5-50 gm/l, Thiamine hydrochloride within a range of 0.002-0.005 gm/l, cysteine within a range of 0.2-0.5 gm/l, and calcium chloride within a range of 0.2-0.5.

9. The method according to claim 8, wherein the feed medium comprises glucose within a range of 100-500 gm/l, yeast extract within a range of 5-50 gm/l, Thiamine hydrochloride within a range of 0.002-0.005 gm/l, cysteine within a range of 0.2-0.5 gm/l, and calcium chloride within a range of 0.2-0.5.

10. The method according to claim 8, wherein the feed medium comprises glucose within a range of 100-200 gm/l, magnesium sulphate within a range of 1-3 gm/l, Hy-soya within a range of 50-150 gm/l and yeast extract within a range of 15-25 gm/l.

11. The method according to claim 1, wherein the concentration of sodium hydroxide in the alkali mixture is between 1.5 and 3.0 M.

12. The method according to claim 1, wherein the concentration of sodium carbonate in the alkali mixture is between 10 and 20% (w/v).

13. The method according to claim 1, wherein said bacteria is selected from *Streptococcus pneumoniae, Neisseria meningitidis, Staphylococcus aureus, Haemophilus influenzae*, and Group A *Streptococcus*.

14. The method according to claim 5, wherein the glucose is converted to lactic acid and the preset pH range is maintained by addition of additional alkali mixture with simultaneous glucose addition to replace the glucose converted to lactic acid.

* * * * *